United States Patent
Kiyoi et al.

(10) Patent No.: US 7,125,659 B1
(45) Date of Patent: Oct. 24, 2006

(54) METHOD AND SCREENING CANDIDATE COMPOUNDS FOR DRUG AGAINST TUMOR

(75) Inventors: Hitoshi Kiyoi, Aichi (JP); Tomoki Naoe, Aichi (JP); Masayuki Towatari, Aichi (JP); Toshio Kitamura, Tokyo (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/763,175

(22) PCT Filed: Aug. 19, 1999

(86) PCT No.: PCT/JP99/04450

§ 371 (c)(1),
(2), (4) Date: May 30, 2001

(87) PCT Pub. No.: WO00/11470

PCT Pub. Date: Mar. 2, 2000

(30) Foreign Application Priority Data

Aug. 20, 1998 (JP) ............................... 10-233729

(51) Int. Cl.
  C12Q 1/00   (2006.01)
  G01N 33/53  (2006.01)
  G01N 33/567 (2006.01)
  A01N 37/18  (2006.01)
  A61K 35/14  (2006.01)

(52) U.S. Cl. .................... 435/4; 435/7.1; 435/7.2; 435/7.21; 435/7.24; 435/7.8

(58) Field of Classification Search ............... 435/4, 435/7.1, 7.2, 7.21, 7.24, 7.8
See application file for complete search history.

(56) References Cited

U.S. PATENT DOCUMENTS 5,635,388 A  6/1997 Bennett et al.

OTHER PUBLICATIONS

Serve et al (Int. J. Oncol., 1999, 14(4)765-770).*
Lemola et al (Blood, 1991, 77:1829-1836).*
Kiyoi et al (Leukemia, 1998, 12:1333-1337).*
Teller etal (Leukemia, 2002, 16:1528-1534).*
Yokota et al (Leukemia, 1997, 11: 1605-1609).*
Carow et al (Blood, 1996, 87:1089-1096).*
Li et al (PNAS, 1992, 89:3315-3319).*
Nakao et al (Leukemia, 1996, 10:1911-1918).*
Yokota et al (Leukemia, 1997, 11:1605-1609.)*
Carow et al (Blood, 1996, 87:1089-1096).*
Li et al (PNAS, 1992, 89:3315-3319).*
S. Yokota et al., Leukemia, "Internal tandem duplication of the FLT3 gene is preferentially seen in acute myeloid leukemia and myelodysplastic syndrome among various hematological malignancies. A study on a large series of patients and cell lines," vol. 11, pp. 1605-1609 (1997) Stockton Press.
H. Kiyoi et al., Leukemia, "Internal tandem duplication of FLT3 associated with leukocytosis in acute promyelocytic leukemia," vol. 11, pp. 1447-1452 (1997) Stockton Press.
M. Nakao et al., "internal tandem duplication of the flt3 gene found in acute myeloid leukemia," vol. 10, pp.1911-1918 (1996) Stockton Press.
Kiyoi et al., "FLT3 in Human Hematologic Malignancies," Leukemia and Lymphoma, vol. 43, No. 8, 2002, Taylor & Francis Ltd., pp. 1541-1547.
Zhao et al., "In Vivo Treatment of Mutant FLT3-Transformed Murine Leukemia with a Tyrosine Kinase Inhibitor," Leukemia, vol. 14, 2000, Macmilan Publishers Ltd., pp. 374-378.

* cited by examiner

*Primary Examiner*—Susan Ungar
(74) *Attorney, Agent, or Firm*—Foley & Lardner LLP

(57) ABSTRACT

Investigation on the frequency of FLT3/ITD found in various blood cancers has revealed that the frequency is high in acute myeloblastic leukemia in particular. Studies on the effects of FLT3/ITD in the blood cell lines revealed that the tyrosine residues in FLT3/ITD is constitutively phosphorylated in these cell lines and that blood cells into which FLT3/ITD is introduced show IL-3 independent proliferation. Moreover, the blood cells into which FLT3/ITD is introduced are found to be capable of forming tumors and inhibit cell differentiation. The inventors have found that it is possible to screen for pharmaceutical compounds against tumors by using inhibition of these FLT3/ITD functions as an index.

2 Claims, 3 Drawing Sheets

METHOD AND SCREENING CANDIDATE COMPOUNDS FOR DRUG AGAINST TUMOR

TECHNICAL FIELD

The present invention relates to a method for screening a candidate compound for a drug against tumors, in particular, blood cancers. More specifically, it relates to a method for screening a compound that inhibits the function of FLT3/ITD in animal cells, including blood cell lines.

BACKGROUND ART

FTL3, as well as KIT, FMS and PDGFR, is a protein of a class III receptor tyrosine kinase (RTK), and is presumed to be involved in the hematopoietic system (Rosnet, O. et al., 1991, Genomics 9:380–385; Rosnet, O. et al., 1991, Oncogene, 6:1641–1650; Matthews, W. et al., 1991, Cell, 65: 1143–1152; Rosnet, O. et al., 1993, Blood, 82: 1110–1119). Structurally, RTK has an extracellular region containing five immunoglobulin-like domains, one juxtamembrane region (JM domain), two tyrosine domains (TK1 and TK2) intervened by a kinase insert domain (KI domain), and the C-terminal domain. FLT3 is strongly expressed in the hematopoietic stem cells as well as the brain, placenta and liver (Rosnet, O. et al., 1991, Oncogene 6:1641–1650; Matthews, W. et al., 1991, Cell, 65: 1143–1152; Rosnet, O. et al., 1993, Blood, 82: 1110–1119; Rusten, L. S., 1996, 87: 1317–1325). A ligand for FLT3 (FL) is expressed from stromal cells in the bone marrow, and present in a membrane-bound or soluble form. This ligand stimulates stem cells independently or together with other cytokines (Hannum, C. et al., 1994, Nature, 368: 643–648; McKenna, H. J. et al., 1995, Blood, 86: 3413–3420; Hirayama, F., 1995, Blood, 85: 1762–1768; Lisovsky, M. et al., 1996, Leukemia, 10: 1012–1018). Therefore, the ligand-receptor interaction between FL and FLT3 is thought to play an important role in the hematopoietic system.

On the other hand, high levels of FLT3 expression are observed in most of the specimens from patients with acute myeloid leukemia (AML) or acute chronic lymphocytic leukemia (ALL). High levels of FLT3 expression are also found in the patients with chronic myeloid leukemia (CML). FL is known to stimulate the proliferation of AML cells more prominently than AML cells (Piacibello, W. et al., 1995, Blood, 86: 4105–4114; Stacchini, A. et al., 1996, Leukemia, 10: 1584–1591; Lisovsky, M. et al., 1996, Blood, 88: 3987–3997; Birg, F. et al., 1992, Blood, 80: 2584–2593, Dehmel, U. et al., 1996, Leukemia, 10: 261–270). This indicates that FLT3 has a function specific to myeloid cells. In several leukemia-lymphoma cell lines, FLT3 and FL are co-expressed (DaSilva, N. et al., 1994, Leukemia, 8: 885–888; Meierhoff, G. 1995, Leukemia, 9: 1368–1372), suggesting their autocrine or paracrine mechanism.

Mutations in cytokine receptors that occur in the process of tumorigenesis have received attention in recent years. To date, mutations in c-fms and c-kit in human leukemia have been reported (Lowenverg, B. and Touw, I. P., 1993, Blood, 81: 281–292). Murine NIH3T3-cells transfected with a mutant c-fms undergo ligand-independent transformation (Roussel, M. et al., 1988, Cell, 55: 979–988). M-CSF, a ligand for fms, increases cell proliferation only slightly in the most of leukemic patients. Thus, the significance of FMS mutation is still unknown (Lowenberg, B. and Touw, I. P., 1993, Blood, 81: 281–292). KIT and its ligand SCF stimulate proliferation of leukemia and stemcells (Lowenberg, B. and Touw, I. P., 1993, Blood, 81: 281–292; Witte, O., 1990, Cell, 63: 5–6). However, mutations in c-kit gene have been found in the mast cell leukemic cell lines, which mutations have not been fully identified in clinical samples (Tsujimura, T. et al., 1994, Blood, 83:2619–2626; Kitayama, H., 1996 Blood, 88: 995–1004; Tsujimura, Y. et al., 1996, Blood, 87: 273–283).

Recently, somatic mutations in FLT3 were found in AML patients (Nakao, M. et al., 1996, Leukemia, 10: 1911–1918). In these mutants, internal tandem duplication (ITD) was found in the region coding for the JM domain of the FLT3 gene. The duplicated sequences predominantly contain exon 11/12 and intron 11, though varying in length in each sample, and they commonly have an extended JM domain which is translatable in a protein due to an extended in-frame open reading frame.

FLT3 mutations are found in about 20% of AML patients and about 3% of patients with myelodysplasia syndrome (MDS), but not in patients with chronic myeloid leukemia (CML) or lymphocytic blood cancer (Yokota, S. et al., 1997, Leukemia 11: 1605–1609). To the inventors' knowledge, mutant FLT3 genes containing ITD (hereinafter referred to as "FLT3/ITD") are found in some AML patients when the tumor recurs, even though they are not found by the early diagnosis, suggesting that FLT3/ITD is responsible for progression of leukemia. However, the role of FLT3/ITD in the progression of leukemia has not been reported so far.

DISCLOSURE OF THE INVENTION

An objective of the present invention is to elucidate the FLT3/ITD function in blood cancers, such as leukemia, and to provide a screening method for a candidate compound for a drug against tumors, such as blood cancer, using inhibition of the FLT3/ITD function as an index.

To solve the problems above, the inventors have investigated the functions of FLT3/ITD in the blood cell lines to find that tyrosine residues present in FLT3/ITD are costitutively phosphorylated in the cell lines tested, that blood cells into which FLT3/ITD is introduced proliferate in an IL-3-independent manner, and that syngeneic mice inoculated with those blood cells develop tumors. These findings suggest that IL-3-independent cell proliferation is induced by proliferative signaling of FLT3/ITD mediated by tyrosine-phosphorylation of FLT/ITD, and that this proliferation, in particular, is responsible for progression of tumors in hematopoietic organs, such as acute myeloid leukemia. Based on these observations, the inventors found that inhibition of FLT3/ITD function can be used as an index to screen for a candidate compound for a drug that can be used in the treatment of blood cancers, etc.

Specifically, the present invention relates to a method for screening a candidate compound for a drug used in the treatment of tumors, using inhibition of FLT3/ITD function in the blood cells as an index. More specifically, the present invention relates to:

(1) a method for screening a candidate compound for an antitumor drug, said method comprising the steps of:

(a) providing animal cells showing cytokine-independent proliferation due to expression of FLT3/ITD, (b) contacting said cells with a test sample and culturing said cells in the absence of cytokines, (c) detecting the proliferation of said cells, and (d) selecting a compound that inhibits the proliferation of said cells;

(2) a method for screening a candidate compound for an antitumor drug, said method comprising the steps of:

(a) providing animal cells showing cytokine-independent proliferation due to expression of FLT3/ITD, (b) contacting said cells with a test sample and culturing said cells in the absence of cytokines, (c) detecting phosphorylation of FLT3/ITD in said cells, and (d) selecting a compound that inhibits the phosphorylation of FLT3/ITD in said cells;

(3) a method for screening a candidate compound for an antitumor drug, said method comprising the steps of:

(a) providing animal cells showing cytokine-independent proliferation due to expression of FLT3/ITD, (b) inoculating a non-human mammal with said cells to develop tumors, (c) administering to said non-human mammal a test sample before or after the inoculation with said cells, and detecting the development of the tumor., and (d) selecting a compound that inhibits the development of the tumor in said non-human mammal;

(4) a method for screening a candidate compound for an antitumor drug, said method comprising the steps of:

(a) providing animal cells in which differentiation-inducing potency is suppressed due to expression of FLT3/ITD, (b) contacting said cells with a test sample and culturing said cells, (c) detecting the differentiation-inducing potency of said cells, and (d) selecting a compound that facilitates differentiation of said cells;

(5) the method according to any one of (1) to (4), wherein said tumor is a blood cancer;

(6) the method according to (5), wherein said blood cancer is acute myeloid leukemia or myelodysplasia syndrome;

(7) the method according to any one of (1) to (3), wherein said cytokine is IL-3;

(8) the method according to any one of (1) to (4), wherein said animal cells are blood cells;

(9) the method according to (8), wherein said blood cells are FDC-P1, 32D, or BaF cells;

(10) the method according to (4), wherein said animal cells are 32D cells; and

(11) a candidate compound for an antitumor drug, wherein said compound can be isolated by the method according to any one of (1) to (10).

As shown in the working examples, tyrosine-phosphorylation of FLT/ITD was detected in the myeloid cell line, FDC-P1 (ATCC CRL-12103), into which FLT3/ITD was introduced (Example 3). In contrast to the parent cell line FDC-P1, which proliferates IL-3-dependently, FDC-P1 cells into which FLT3/ITD was introduced were found to proliferate IL-3-independently (Example 4). These facts have shown for the first time that tandem duplicate mutation in FLT3 is functionally related to tumorigenesis of blood cells. The inventors have found it possible to inhibit aberrant cell growth and to treat tumors including those found in hematopoietic organs, for example, leukemia, by blocking the FLT3/ITD function as described above.

One embodiment of the present invention is a method for screening a candidate compound for a drug against tumors, such as blood cancers, using as an index inhibition of the proliferation of animal cells, such as blood cells, in which FLT3/ITD is expressed. Specifically, this method comprises the steps of (a) providing animal cells that proliferate cytokine-independently due to the expression of FLT3/ITD, (b) contacting said cells with a test sample and culturing said cells in the absence of cytokines, (c) detecting the proliferation of said cells, and (d) selecting a compound that inhibits said cell proliferation.

Another embodiment of the present invention is a method for screening a candidate compound for a drug against tumors, such as blood cancers, using as an index inhibition of tyrosine-phosphorylation of FLT3/ITD in blood cells, etc. Specifically, this method comprises the steps of (a) providing animal cells that proliferates cytokine-independently due to expression of FLT3/ITD, (b) contacting said cells with a test sample and culturing said cells in the absence of cytokines, (c) detecting phosphorylation of FLT3/ITD in said cells, and (d) selecting a compound that inhibits the phosphorylation of FLT3/ITD in said cells.

Another embodiment of the present invention is a method for screening a candidate compound for a drug against tumors, such as blood cancers, using as an index inhibition of tumorigenesis in animal cells, such as blood cells, in which FLT3/ITD is expressed. Specifically, this method comprises the steps of (a) providing animal cells that proliferate cytokine-independently due to expression of FLT3/ITD, (b) inoculating a non-human mammal with said cells to develop tumors, (c) administering to said non-human mammal a test sample before or after the inoculation with said cells, and detecting the development of the tumor, and (d) selecting a compound that inhibits the development of the tumor in said non-human mammal.

Yet another embodiment of the present invention is a method for screening a candidate compound for a drug against tumors, such as blood tumors, using as an index differentiation-inducing potency, i.e. an effect that facilitates cell differentiation, of animal cells, such as blood cells, in which FLT3/ITD is expressed. Specifically, this method comprises the steps of (a) providing animal cells in which differentiation-inducing potency is suppressed due to expression of FLT3/ITD, (b) contacting said cells with a test sample and culturing said cells, (c) detecting the differentiation-inducing potency of said cells, and (d) selecting a compound that facilitates differentiation of said cells. Compounds that facilitate cell differentiation include compounds that stimulate the cell differentiation by themselves or together with other cytokines that are known to stimulate the cell differentiation.

The tumors targeted by drug candidate compounds screened by the method of the present invention include any tumors that are caused by internal tandem duplication (ITD) of FLT3, inter alia, blood cancers, for example, acute myeloid leukemia and myelodysplasia syndrome. In particular, acute myeloid is the most preferable as a target disease.

Test samples used in the screening include, but are not limited to, purified proteins (including antibodies), expression products from a gene library, a library of synthetic peptides, cell extracts, cell culture supernatant, a library of synthetic low-molecular-weight compounds, oligonucleotides, etc.

Any animal cell can be used as the cells used for the screening as long as it proliferates cytokine-independently or has suppressed differentiation-inducing potency due to the FLT3/ITD expression. Blood cells (including hematopoietic stem cells) are preferable. Such cells include, for example, FDC-P1 cells (ATCC: CRL-12103) (American Type Culture Collection P.O. Box 1549, Manassas, Va. 20108, USA) 32D cells (RIKEN (The Institute of Physical and Chemical Research, 3-1-1 Koyadai, Tsukuba, Ibaraki, 305-0074 Japan) Cell Bank: RCB 1145), Ba/F3 cells (RIKEN Cell Bank: RCB 0805), DA-3 cells (RIKEN Cell Bank: RCB 1144), all of which show IL3-dependent cell proliferation. Among them, in particular, FDC-P1, 32D, and Ba/F3 cells are preferable. Intracellular expression of FLT3/ITD can be carried out by means of a genetic engineering technique well known to those skilled in the art. Any FLT3/ITD can be used for its expression in the cell, as long as it induces the proliferation of blood cells in a cytokine-independent manner. Such FLT3/ITD includes, for example, FLT3/ITD comprising any one of the amino acid sequences of SEQ ID NO: 2, 4, 6 and 8. The FLT3/ITD sequences described in the literatures (Yokota, S. et al. 1997, Leukemia 11: 1605–1609; Kiyoi, H. et al. 1997, Leukemia 11: 1447–1452) can be used in this invention. In addition, FLT3/ITD newly obtained from patients with blood cancer can also be used. FLT3/ITD may be synthesized artificially or derived from cells.

Test samples can be contacted with cells by the method suitable to the samples used, for example, by the method in which a test sample is added to the cell culture medium or the method in which a test sample is introduced into the cells.

The followings are specific examples of the screening methods of the present invention, but they are not construed to limit the scope of the present invention.

(i) Wild type FLT3 or FLT3/ITD is inserted into a commercially available expression vector carrying a selectable marker such as a neomycin resistance gene, and the vector is introduced into cells, such as FDC-P1 and 32D cells, with an apparatus, such as Bio-Rad Gene Pulser Cuvettes (Bio-Rad). The cells transfected with FLT3/ITD are selected, seeded onto a 24-well plate to approximately $5\times10^4$ cells, and cultured in a $CO_2$ incubator at 37° C. in the presence or absence of a test sample. Two or three days later, viable cells are counted by trypan blue staining, MTT assay, or other assays, to select a compound that inhibits the cell proliferation.

(ii) Wild type FLT3 or FLT3/ITD is inserted into a commercially available expression vector carrying a selectable marker such as a neomycin resistance gene, and the vector is introduced into cells, such as FDC-P1 and 32D cells, with an apparatus, such as Bio-Rad Gene Pulser Cuvettes (Bio-Rad). The cells transfected with FLT3/ITD are selected and seeded onto a 10-cm plate to approximately $1\times10^6$ cells. [γ-32P]ATP is added to the plate. The cells are cultured in the presence or absence of a test sample in a $CO_2$ incubator at 37° C. Subsequently, the cell extract is prepared and immunoprecipitated with anti-FLT3 antibody and anti-phosphorylated-tyrosine antibody, followed by electrophoresis and autoradiography to detect the radioisotope incorporated in FLT3/ITD. A compound that inhibits tyrosine-phosphorylation of FLT3 can thus be selected.

(iii) Approximately $2\times10^7$ FDC-P1 cells transfected with FLT3/ITD by the method described above in (i) are inoculated subcutaneously to DBA2 mice. FDC-P1 cells were established from this mouse strain. About two weeks after the inoculation, the mice developed tumors. FLT3/ITD expression in the tumors formed was identified in DNA and protein levels (FIGS. 3A and B). The tumors were developed without any particular treatment, such as irradiation. That is, the cells, including blood cells, which are transfected with FLT3/ITD, can develop tumors by the action of FLT3/ITD when they are inoculated to non-human mammals, such as syngeneic mice. Therefore, a compound that can inhibit the tumorigenesis can be selected by administering a test sample percutaneously, intravenously or orally before or after the inoculation of the cells, such as blood cells, which are transfected with FLT3/ITD, and examining their effect on the development and elimination of the tumors.

(iv) The inventors have found that 32D cells, for example, are IL3-dependent cells and their differentiation are induced in the presence of G-CSF, and that the G-CSF-induced differentiation is inhibited when FLT3/ITD is introduced into the cells. On the basis of this knowledge, the following method has been developed. Approximately $5\times10^4$ cells of the transformed cells, such as blood cells that are transfected with wild type FLT3 or FLT3/ITD by the method described above in (i) are seeded onto a 24-well plate. Cytospin samples are prepared at various time points after adding a test sample to examine their potential for differentiation by staining with May-Giemsa, peroxidase, esterase, alkaline phosphatase, etc. or by flow cytometry to determine the expression of CD11b, CD13, CD14 and CD33, etc. A compound that promotes the differentiation-inducing potency of the cells can thus be selected.

To eliminate the effects of nonselective cytotoxic substances in the screening system in which cell proliferation is used as an index, the parent cells are cultured in the presence of IL-3 and a test sample is added to the culture to determine the effects of the test sample on IL-3-dependent cell-proliferation in parallel with the experiment above.

The compounds that can be isolated through the screening of the present invention may vary in their activities. Examples of the compounds include, for example, those inhibiting the function of FLT3/ITD through the direct action thereon, those indirectly inhibiting the FLT3/ITD function by acting on a molecule that binds to FLT3/ITD or phosphorylated FLT3/ITD (e.g. adapter proteins, such as SHC, Grb2, Cb1, PI3K, RAS-GAP and PLC-γ), those acting on a group of proteins that is involved in the signal transduction pathway from FLT/ITD up to cell proliferation, those acting on a protein that can phosphorylate FLT3/ITD and inhibiting the function thereof, those acting on a group of proteins that is involved in the signal transduction pathway from FLT/ITD to cause its phosphorylation, and those dephosphorylating FTL3/ITD that is constitutively phosphorylated.

These compounds are candidates for a drug to treat tumors, such as blood cancers, in the development which FLT3/ITD is involved. Among the compounds screened, the compounds that specifically inhibit the FLT3/ITD function but not inhibit the function of wild type FLT3 are preferable as candidates for drugs to specifically treat the diseases mentioned above caused by FLT3/ITD.

When a compound isolated by the screening method of the present invention is used as a drug, it can be formulated by any pharmaceutical manufacturing methods well known in the art. For example, the drug is combined with a pharmaceutically acceptable carrier or medium (e.g. saline, vegetable oil, suspending agent, surfactant, stabilizer, etc.) and administered to patients. The drug can be administered via various routes, for example, percutaneously, intranasally, transbronchially, intramuscularly, intravenously, or orally, depending on the properties of the compound. Dosage may vary depending on the factors, such as age, weight, condition of the patient and the administration method, but those skilled in the art can properly determine the suitable dosage.

BEST MODE FOR CARRYING OUT THE INVENTION

Figure 1:
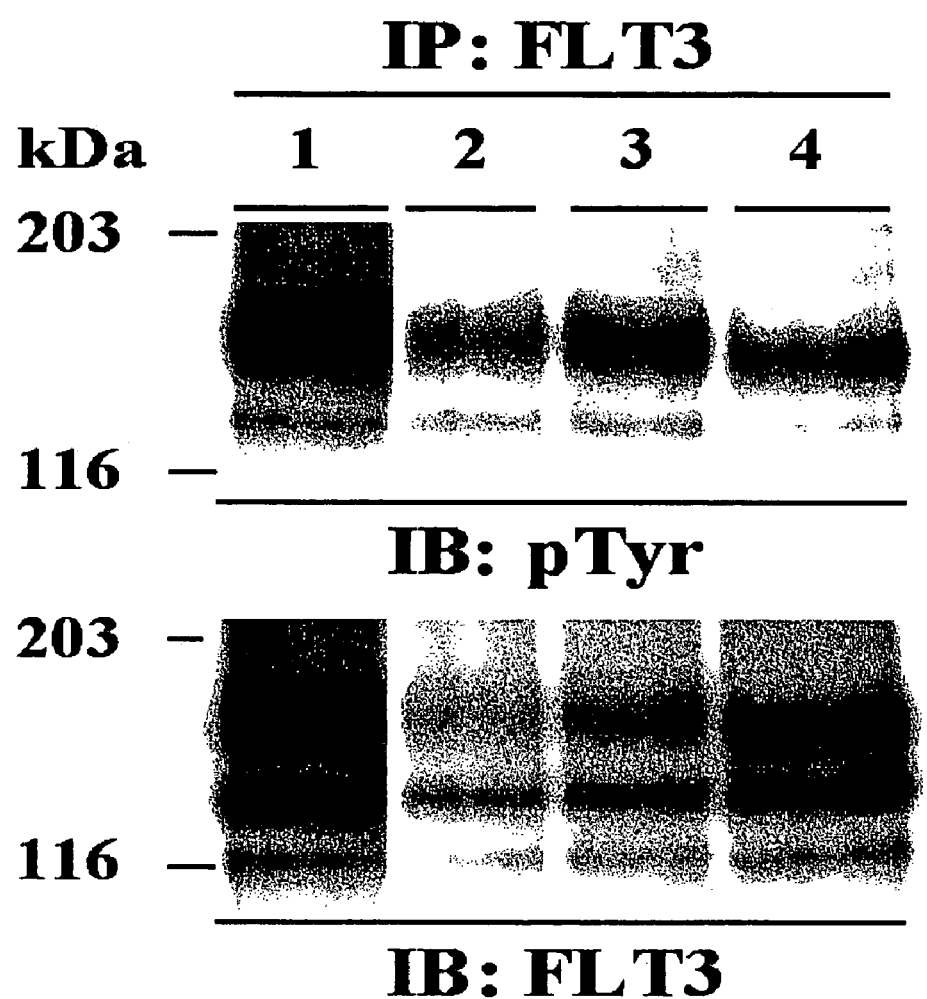
FIG. 1 shows tyrosine-phosphorylation of FLT3 protein in FDC-P1 cells into which wild type FLT3 or FLT3/ITD has been introduced. The cell extracts were immunoprecipitated with anti-FLT3 antibody (IP: FLT3), resolved by SDS-PAGE, and subjected to Western blotting with anti-phosphorylated-tyrosine antibody (Upper panel, IB: pTyr). The same membrane was further subjected to Western blotting using anti-FLT3 antibody (Lower Panel, IB:FLT3). Lane 1, Mt1; Lane 2, Mt2; Lane 3, Mt3; and Lane 4, Mt4.

The present invention will be explained in detail below with reference to examples, but is not to be construed as being limited thereto. Unless otherwise mentioned, "FLT3" used herein represents mutant FLT3 including FLT3/ITD as well as wild type FLT3. The term "aberrant FLT3" refers to any abnormalities of FLT3 including not only expression of mutant to FLT3 but also overexpression of wild type FLT3.

EXAMPLE 1

Detection of FLT3/ITD in Leukemia Cells

High molecular weight DNA was isolated from leukemia cells, and a DNA fragment containing the JM domain of the FLT3 protein was amplified by PCR according to the method described in Kiyoi, H., Leukemia 11: 1447–1452, 1997. The bands that differed from the band of the wild-type in size were excised from agarose gel and purified with Qiaex gel extraction kit (Qiagen), followed by cloning into pMOSBlue T vector (Amersham) according to the manufacturer's instruction. Ten colonies of the recombinants were cultured on the LB medium, and the plasmid DNA was prepared with QIAprep spin plasmid miniprep kit (QIAGEN). Nucleotide sequences of these clones were confirmed by sequencing. Expression of the FLT3 mRNA was confirmed by RT-PCR according to the method described in Kiyoi, H., Leukemia 11: 1447–1452, 1997. The bands that differed from the band of the wild type in size were cloned according to the method described above, and their nucleotide sequences were confirmed by sequencing.

The results are summarized in Table 1 showing the frequency of FLT3/ITD within various blood cancers (the number of cases in which FLT3/ITD was detected/the total number of cases tested).

TABLE 1

| Diagnosis | Frequency |
|---|---|
| ALL | 0/48 |
| ATL | 0/14 |
| CLL | 0/15 |
| ET | 0/3 |
| ML | 0/16 |
| MM | 0/38 |
| Histiocytosis | 0/1 |

TABLE 1-continued

| Diagnosis | Frequency |
|---|---|
| CML-BC | 0/13 |
| CMMoL | 0/17 |
| MDS | 1/15 |
| AML (total) | 35/221 |
| M0 | 0/2 |
| M1 | 5/18 |
| M2 | 4/29 |
| M3 | 16/124 |
| M4 | 6/24 |
| M5 | 4/20 |
| M6 | 0/1 |
| M7 | 0/3 |

It was confirmed that among various blood cancers, FLT3/ITD is specifically found in AML; its percent frequency was so high as about 20%. FLT3/ITD was also found in MDS, but its percent frequency was so low as about 3%.

EXAMPLE 2

Introduction of an FLT3/ITD Expression Vector into Blood Cells

Total RNA was extracted from leukemia cells and was used for cDNA synthesis. The cDNA synthesized was used as a template to amplify the MunI-EcoRV fragment, which contains the tandem repeat region found in mutants FTL3 cDNA, by RT-PCR. MunI-F primer (SEQ ID NO: 9/5'-CAACAATTGGTGTTTGTCTCCTCTT-3') and EcRV-R primer (SEQ ID NO: 10/5'-CATGATATCTCGAGC-CAATCCAAAG-3') were used for the amplification. The amplified fragments were cleaved with MunI and EcoRV (Boehringer-Mannheim-Yamanouchi), resolved on agarose gel, and purified according to the aforementioned method. Expression vector pCDHF3 (a gift from Dr. Olivier Rosnet), which carries a full-length wild type FLT3 cDNA (Rosnet, O. et al., Blood 82:1110–1119; Accession No. S64785), was cleaved with MunI and EcoRV, and the purified FLT3/ITD fragment was inserted into the vector. Four mutants of FLT3/ITD (Mt1, Mt2, Mt3 and Mt4) were used. Nucleotide sequences of the mutated regions of Mt1 to Mt4 are shown as SEQ ID NOs. 1, 3, 5 and 7, and their amino acid sequences are shown as SEQ ID NOs. 2, 4, 6 and 8, respectively. Expression vectors for Mt1 to Mt4 were transfected into the blood cells.

FLT3/ITD expression plasmids thus obtained were introduced into blood cells as follows. The cells were co-transfected with a 10:1 mixture of any one of the expression plasmids and pBabe-neo vector (Nucleic Acids Res., 18:3587–3596, 1990) by using Bio-Rad Gene Pulser Cuvettes (Bio-Rad; 300 V, 960 µF), and selected with 800 ng/ml neomycin. After cloning, FLT3 expressions of the cloned cells were verified by FACS and Western blotting to establish the transfected clones.

FLT3/ITD genes were introduced into a myeloid cell line, FDC-P1 cells.

EXAMPLE 3

Tyrosine-Phosphorylation of the FLT3 Molecules in the Transfectants (1) The transfectants were cultured in RPMI 1640 medium supplemented with 10% FCS (GIBCO), and then centrifuged at 1000 rpm for 5 minutes to recover $2 \times 10^7$ cells. The cell pellets were washed with PBS, dissolved in lysis buffer (20 mM Tris-HCl, pH 7.5, 150 mM NaCl, 2 mM EDTA, Nonidet P-40, 50 mM NaF, 10 mg/ml aprotinin, 10 mg/ml leupeptin, 1 mM $Na_3VO_4$, 50 mM $Na_2MoO_4$, 1 mM phenylmethylsulfonyl fluoride (PMSF)), allowed to stand for 1 hour at 4° C., then centrifuged at 15000 rpm for 30 minutes. Rabbit anti-human FLT3 antibody (Santa Cruz Biotechnology, Santa Cruz, Calif., USA) was added to the supernatants and the mixture was stirred for 2 hours at 4° C. After adding Protein A/G Plus agarose (Santa Cruz), the resulting mixture was stirred for 2 hours at 4° C. and washed with the lysis buffer three times. The pellets were then dissolved in sample loading buffer (0.125 M Tris-HCl, pH 6.8, 10% 2-mercaptoethanol, 4% SDS), subjected to SDS-PAGE, transferred onto Immobilon PVDF membrane (Millipore), and reacted with anti-phosphorylated tyrosine antibody (4G10, Upstate Biotechnology, Lake Placid, N.Y., USA). Following the reaction, the bands were detected using the ECL system (Amersham). To confirm the presence of FLT3 protein, the same membrane was incubated in stopping buffer (100 mM 2-mercaptoethanol, 2% SDS, 62.5 mM Tris-HCl, pH 6.8) for 30 minutes at 70° C., and then reacted with rabbit anti-human FLT3 antibody.

The results for FDC-P1 cells are shown in FIG. 1. As shown in this figure, all the FLT3/ITDs introduced into FDC-P1 cells were phosphorylated at the tyrosine residues, indicating that a signaling pathway for tyrosine-phosphorylation of FLT3/ITD is constitutively activated. On the contrary, wild type FLT3 protein was not phosphorylated in the absence of FL.

The same result was obtained for 32D cells.

EXAMPLE 4

Proliferation Properties of FLT3/ITD-Introduced Cells

FDC-P1 cells ($5 \times 10^4$ cells) into which wild type FLT3 (wt) or FLT3/ITD (Mt1 to Mt4) was introduced were cultured in the four media indicated below on a 24-well plate at 37° C. in a $CO_2$ incubator.

Figure 2:
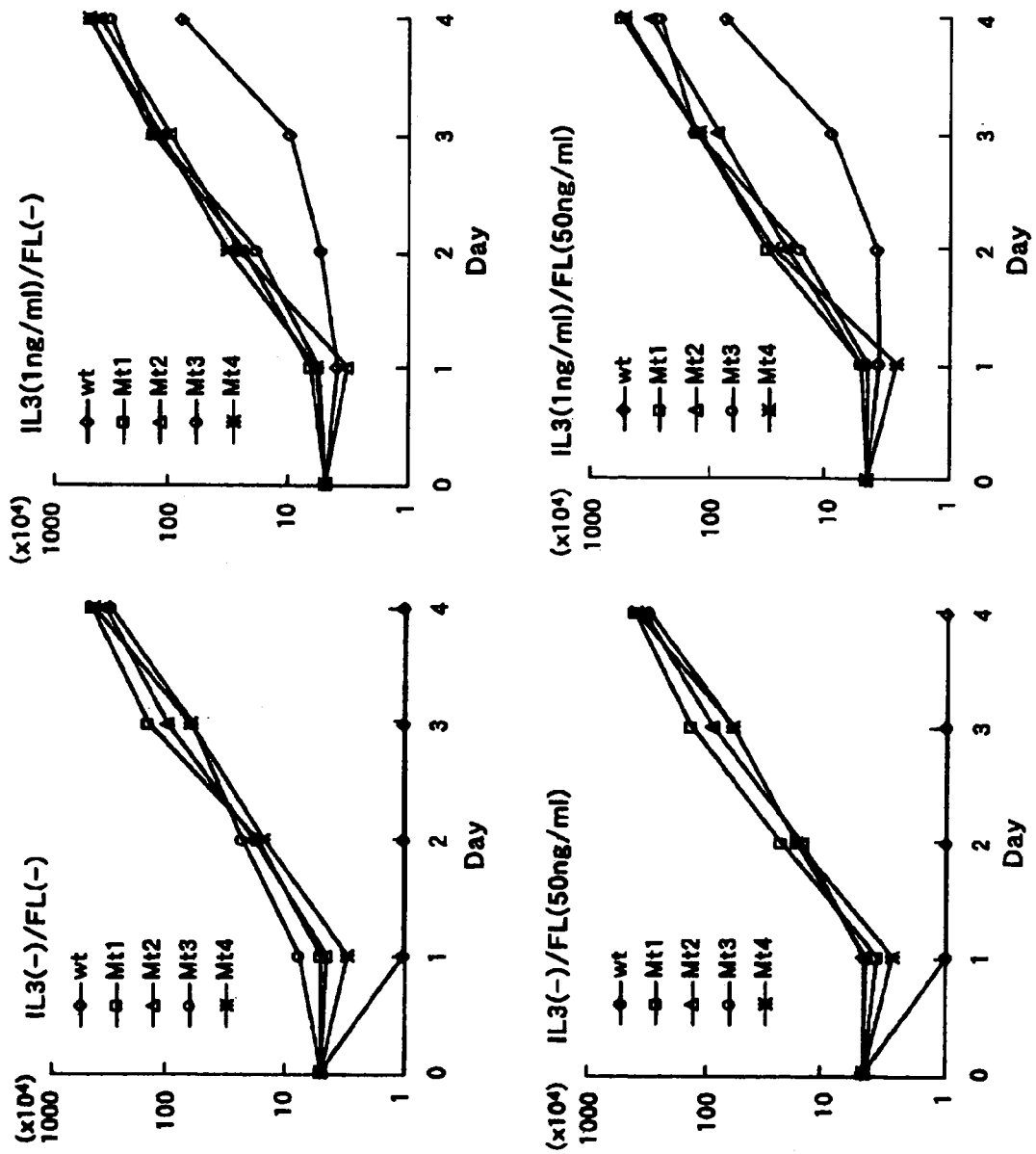
FIG. 2 shows the proliferation properties of FDC-P1 cells into which wild type FLT3 or one of four FLT3/ITD mutants has been introduced. Each mutant was cultured in the absence of IL-3 and FL (Upper left graph, IL3(−)/FL(−)); in the presence of IL-3 (1 ng/ml) (Upper right graph, IL3(1 ng/ml)/FL(−)); in the presence of FL (50 ng/ml) (Lower left graph, IL-3(−)/FL (50 ng/ml)); and in the presence of both IL-3 and FL (Lower right, IL-3 (1 ng/ml)/FL (50 ng/ml)).
Figure 3:
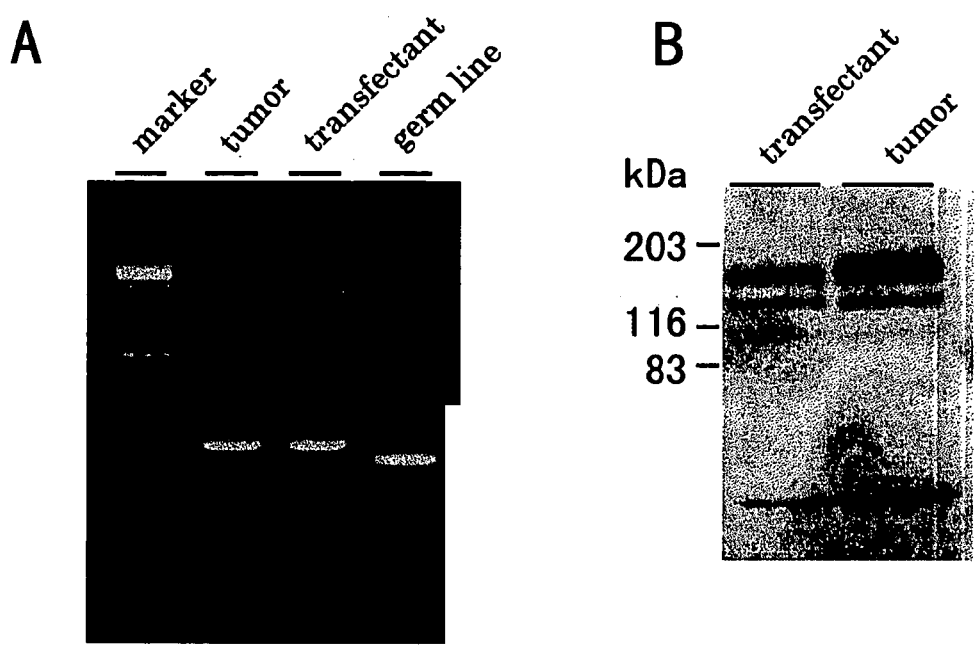
FIG. 3 shows the presence of FLT3/ITD DNA and the expression of its protein in the tumors formed in DBA2 mice that were subcutaneously inoculated with FDC-P1 cells into which FLT3/ITD was introduced. Panel A shows the DNA bands amplified by PCR and resolved by electrophoresis, indicating the presence of FLT3/ITD DNA in the tumors. Panel B shows the results of Western blotting of the whole cell extracts using anti-FLT antibody, indicating the presence of FLT3/ITD protein in the tumors.

1. RPMI1640 supplemented with 10% FCS alone (FIG. 2, upper left graph);

2. RPMI1640 supplemented with 10% FCS+1 ng/ml mouse IL-3 (Genzyme) (FIG. 2, upper right graph);

3. RPMI1640 supplemented with 10% FCS+50 ng/ml human FL (Purotech) (FIG. 2, lower left graph);

4. RPMI1640 supplemented with 10% FCS+1 ng/ml mouse IL-3+50 ng/ml human FL (FIG. 2. lower right graph).

The cells were stained with trypan blue and the viable cells were counted at 24-hour intervals for 4 days to determine the proliferation potency of each cell line. The results are shown in FIG. 2. As shown in the figure, the cells into which wild type FLT3 is introduced were not able to proliferate in the absence of IL-3, and this IL-3 dependency did not alter even after FL, a ligand for FLT3, was added to the medium. Also, synergistic effect of IL-3 and FL was not observed. In contrast, the cells into which FLT3/ITD was introduced proliferated at an equivalent level irrespective of the presence of IL-3, and their proliferation rate was significantly higher than that of the cells into which wild type FLT3 is introduced in the presence IL-3. Also, neither proliferation promoting effect nor synergistic effect of IL-3 and FL were found in these cells.

These data reveal that FLT3/ITD activates intracellular signaling pathways and triggers cytokine-independent proliferation in the myeloid cells.

The same results were obtained for 32D cells.

INDUSTRIAL APPLICABILITY

The present invention provides a method for screening candidate compounds for drug against tumors, such as blood cancers, using inhibition of FLT3/ITD function as an index. Compounds to be isolated by the method of the present invention could have an inhibitory effect on aberrant proliferation of cells, such as blood cells, caused by FLT3/ITD expression found in blood cancers, in particular, acute myeloid leukemia, and can thus be utilized for development of pharmaceuticals for these diseases.

The invention claimed is:

1. A method for screening a candidate compound for a drug for the treatment of acute myeloid leukemia or myelodysplasia syndrome whose cells express FLT3/ITD, said method comprising the steps of:
   (a) introducing the FLT3/ITD gene into blood cells or hematopoietic stem cells, wherein whereupon said cells express FLT3/ITD and proliferate IL-3 independently;
   (b) contacting said cells with said candidate compound and culturing said cells in the absence of IL-3;
   (c) detecting the proliferation of said cells;
   (d) determining if the candidate compound inhibits the proliferation of said cells by inhibiting FT3/ITD function; and
   (e) selecting the candidate compound that inhibits the proliferation of said cells by inhibiting FLT3/ITD function as a candidate compound for a drug to treat acute myeloid leukemia or myelodysplasia syndrome.

2. The method according to claim 1, wherein said cells into which the FLT3/ITD gene is introduced so as to express FLT3/ITD are FDC-P1, 32D, or BaF cells.

* * * * *

UNITED STATES PATENT AND TRADEMARK OFFICE
CERTIFICATE OF CORRECTION

PATENT NO. : 7,125,659 B1
APPLICATION NO. : 09/763175
DATED : October 24, 2006
INVENTOR(S) : Hitoshi Kiyoi et al.

It is certified that error appears in the above-identified patent and that said Letters Patent is hereby corrected as shown below:

Claim 1, col. 17, line 44, delete "wherein".

Claim 1, col. 18, line 39, "FT3/ITD" should be --FLT3/ITD--.

Signed and Sealed this

First Day of May, 2007

JON W. DUDAS
*Director of the United States Patent and Trademark Office*

SEQUENCE LISTING

```
<160> NUMBER OF SEQ ID NOS: 10

<210> SEQ ID NO 1
<211> LENGTH: 319
<212> TYPE: DNA
<213> ORGANISM: Homo sapiens
<220> FEATURE:
<221> NAME/KEY: CDS
<222> LOCATION: (1)..(318)
<223> OTHER INFORMATION: FLT3/ITD gene (Mt1); partial sequence

<400> SEQUENCE: 1 caa ttt agg tat gaa agc cag cta cag atg gta cag gtg acc ggc tcc      48
Gln Phe Arg Tyr Glu Ser Gln Leu Gln Met Val Gln Val Thr Gly Ser
  1               5                  10                  15 tca gat aat gag tac ttc tac gtt gat ttc aga gaa tat gaa tat gat      96
Ser Asp Asn Glu Tyr Phe Tyr Val Asp Phe Arg Glu Tyr Glu Tyr Asp
             20                  25                  30 ctc aaa tgg gag ttt cca aga gaa aat tgc tcc tca gat aat gag tac     144
Leu Lys Trp Glu Phe Pro Arg Glu Asn Cys Ser Ser Asp Asn Glu Tyr
```

```
                    35                  40                  45
ttc tac gtt gat ttc aga gaa tat gaa tat gat ctc aaa tgg gag ttt      192
Phe Tyr Val Asp Phe Arg Glu Tyr Glu Tyr Asp Leu Lys Trp Glu Phe
    50                  55                  60 cca aga gaa aat tta gag ttt ggg aag gta cta gga tca ggt gct ttt      240
Pro Arg Glu Asn Leu Glu Phe Gly Lys Val Leu Gly Ser Gly Ala Phe
65                  70                  75                  80 gga aaa gtg atg aac gca aca gct tat gga att agc aaa aca gga gtc      288
Gly Lys Val Met Asn Ala Thr Ala Tyr Gly Ile Ser Lys Thr Gly Val
                85                  90                  95 tca atc cag gtt gcc gtc aaa atg ctg aaa g                            319
Ser Ile Gln Val Ala Val Lys Met Leu Lys
            100                 105

<210> SEQ ID NO 2
<211> LENGTH: 106
<212> TYPE: PRT
<213> ORGANISM: Homo sapiens
<220> FEATURE:
<223> OTHER INFORMATION: FLT3/ITD (Mt1); partial sequence
      ITD region (42)..(68)

<400> SEQUENCE: 2

Gln Phe Arg Tyr Glu Ser Gln Leu Gln Met Val Gln Val Thr Gly Ser
 1               5                  10                  15

Ser Asp Asn Glu Tyr Phe Tyr Val Asp Phe Arg Glu Tyr Glu Tyr Asp
                20                  25                  30

Leu Lys Trp Glu Phe Pro Arg Glu Asn Cys Ser Ser Asp Asn Glu Tyr
            35                  40                  45

Phe Tyr Val Asp Phe Arg Glu Tyr Glu Tyr Asp Leu Lys Trp Glu Phe
        50                  55                  60

Pro Arg Glu Asn Leu Glu Phe Gly Lys Val Leu Gly Ser Gly Ala Phe
65                  70                  75                  80

Gly Lys Val Met Asn Ala Thr Ala Tyr Gly Ile Ser Lys Thr Gly Val
                85                  90                  95

Ser Ile Gln Val Ala Val Lys Met Leu Lys
            100                 105

<210> SEQ ID NO 3
<211> LENGTH: 298
<212> TYPE: DNA
<213> ORGANISM: Homo sapiens
<220> FEATURE:
<221> NAME/KEY: CDS
<222> LOCATION: (1)..(297)
<223> OTHER INFORMATION: FLT3/ITD gene (Mt2); partial sequence

<400> SEQUENCE: 3 caa ttt agg tat gaa agc cag cta cag atg gta cag gtg acc ggc tcc      48
Gln Phe Arg Tyr Glu Ser Gln Leu Gln Met Val Gln Val Thr Gly Ser
 1               5                  10                  15 tca gat aat gag tac ttc tac gtt gat ttc aga gaa tat gaa tat gat      96
Ser Asp Asn Glu Tyr Phe Tyr Val Asp Phe Arg Glu Tyr Glu Tyr Asp
                20                  25                  30 ctc aaa agc tcc tca gat aat gag tac ttc tac gtt gat ttc aga gaa     144
Leu Lys Ser Ser Ser Asp Asn Glu Tyr Phe Tyr Val Asp Phe Arg Glu
            35                  40                  45 tat gaa tat gat ctc aaa tgg gag ttt cca aga gaa aat tta gag ttt     192
Tyr Glu Tyr Asp Leu Lys Trp Glu Phe Pro Arg Glu Asn Leu Glu Phe
        50                  55                  60 ggg aag gta cta gga tca ggt gct ttt gga aaa gtg atg aac gca aca     240
```

```
Gly Lys Val Leu Gly Ser Gly Ala Phe Gly Lys Val Met Asn Ala Thr
 65                  70                  75                  80 gct tat gga att agc aaa aca gga gtc tca atc cag gtt gcc gtc aaa      288
Ala Tyr Gly Ile Ser Lys Thr Gly Val Ser Ile Gln Val Ala Val Lys
                 85                  90                  95 atg ctg aaa g                                                        298
Met Leu Lys
```

<210> SEQ ID NO 4
<211> LENGTH: 99
<212> TYPE: PRT
<213> ORGANISM: Homo sapiens
<220> FEATURE:
<223> OTHER INFORMATION: FLT3/ITD (Mt2); partial sequence
      ITD region (35)..(54)

<400> SEQUENCE: 4

```
Gln Phe Arg Tyr Glu Ser Gln Leu Gln Met Val Gln Val Thr Gly Ser
  1               5                  10                  15

Ser Asp Asn Glu Tyr Phe Tyr Val Asp Phe Arg Glu Tyr Glu Tyr Asp
                 20                  25                  30

Leu Lys Ser Ser Ser Asp Asn Glu Tyr Phe Tyr Val Asp Phe Arg Glu
             35                  40                  45

Tyr Glu Tyr Asp Leu Lys Trp Glu Phe Pro Arg Glu Asn Leu Glu Phe
 50                  55                  60

Gly Lys Val Leu Gly Ser Gly Ala Phe Gly Lys Val Met Asn Ala Thr
 65                  70                  75                  80

Ala Tyr Gly Ile Ser Lys Thr Gly Val Ser Ile Gln Val Ala Val Lys
                 85                  90                  95

Met Leu Lys
```

<210> SEQ ID NO 5
<211> LENGTH: 271
<212> TYPE: DNA
<213> ORGANISM: Homo sapiens
<220> FEATURE:
<221> NAME/KEY: CDS
<222> LOCATION: (1)..(270)
<223> OTHER INFORMATION: FLT3/ITD gene (Mt3); partial sequence

<400> SEQUENCE: 5

```
caa ttt agg tat gaa agc cag cta cag atg gta cag gtg acc ggc tcc      48
Gln Phe Arg Tyr Glu Ser Gln Leu Gln Met Val Gln Val Thr Gly Ser
  1               5                  10                  15 tca gat aat gag tac ttc tac gtt gat ttc aga gaa tat gaa atg gga      96
Ser Asp Asn Glu Tyr Phe Tyr Val Asp Phe Arg Glu Tyr Glu Met Gly
                 20                  25                  30 atg ggg gga gaa tgt aat ccc ggg aga caa gat ctc aaa tgg gag ttt     144
Met Gly Gly Glu Cys Asn Pro Gly Arg Gln Asp Leu Lys Trp Glu Phe
             35                  40                  45 cca aga gaa aat tta gag ttt ggg aag gta cta gga tca ggt gct ttt     192
Pro Arg Glu Asn Leu Glu Phe Gly Lys Val Leu Gly Ser Gly Ala Phe
 50                  55                  60 gga aaa gtg atg aac gca aca gct tat gga att agc aaa aca gga gtc     240
Gly Lys Val Met Asn Ala Thr Ala Tyr Gly Ile Ser Lys Thr Gly Val
 65                  70                  75                  80 tca atc cag gtt gcc gtc aaa atg ctg aaa g                           271
Ser Ile Gln Val Ala Val Lys Met Leu Lys
                 85                  90
```

<210> SEQ ID NO 6

```
<211> LENGTH: 90
<212> TYPE: PRT
<213> ORGANISM: Homo sapiens
<220> FEATURE:
<223> OTHER INFORMATION: FLT3/ITD (Mt3); partial sequence
      ITD region (31)..(42)

<400> SEQUENCE: 6

Gln Phe Arg Tyr Glu Ser Gln Leu Gln Met Val Gln Val Thr Gly Ser
 1               5                  10                  15

Ser Asp Asn Glu Tyr Phe Tyr Val Asp Phe Arg Glu Tyr Glu Met Gly
                20                  25                  30

Met Gly Gly Glu Cys Asn Pro Gly Arg Gln Asp Leu Lys Trp Glu Phe
            35                  40                  45

Pro Arg Glu Asn Leu Glu Phe Gly Lys Val Leu Gly Ser Gly Ala Phe
        50                  55                  60

Gly Lys Val Met Asn Ala Thr Ala Tyr Gly Ile Ser Lys Thr Gly Val
 65                 70                  75                  80

Ser Ile Gln Val Ala Val Lys Met Leu Lys
                85                  90

<210> SEQ ID NO 7
<211> LENGTH: 271
<212> TYPE: DNA
<213> ORGANISM: Homo sapiens
<220> FEATURE:
<221> NAME/KEY: CDS
<222> LOCATION: (1)..(270)
<223> OTHER INFORMATION: FLT3/ITD gene (Mt4); partial sequence

<400> SEQUENCE: 7 caa ttt agg tat gaa agc cag cta cag atg gta cag gtg acc ggc tcc      48
Gln Phe Arg Tyr Glu Ser Gln Leu Gln Met Val Gln Val Thr Gly Ser
 1               5                  10                  15 tca gat aat gag tac ttc tac gtt gat ttc aga gaa tat gat gag tac      96
Ser Asp Asn Glu Tyr Phe Tyr Val Asp Phe Arg Glu Tyr Asp Glu Tyr
                20                  25                  30 ttc tac gtt gat ttc aga gaa tat gaa tat gat ctc aaa tgg gag ttt     144
Phe Tyr Val Asp Phe Arg Glu Tyr Glu Tyr Asp Leu Lys Trp Glu Phe
            35                  40                  45 cca aga gaa aat tta gag ttt ggg aag gta cta gga tca ggt gct ttt     192
Pro Arg Glu Asn Leu Glu Phe Gly Lys Val Leu Gly Ser Gly Ala Phe
        50                  55                  60 gga aaa gtg atg aac gca aca gct tat gga att agc aaa aca gga gtc     240
Gly Lys Val Met Asn Ala Thr Ala Tyr Gly Ile Ser Lys Thr Gly Val
 65                 70                  75                  80 tca atc cag gtt gcc gtc aaa atg ctg aaa g                           271
Ser Ile Gln Val Ala Val Lys Met Leu Lys
                85                  90

<210> SEQ ID NO 8
<211> LENGTH: 90
<212> TYPE: PRT
<213> ORGANISM: Homo sapiens
<220> FEATURE:
<223> OTHER INFORMATION: FLT3/ITD (Mt4); partial sequence
      ITD region (30)..(40)

<400> SEQUENCE: 8

Gln Phe Arg Tyr Glu Ser Gln Leu Gln Met Val Gln Val Thr Gly Ser
 1               5                  10                  15

Ser Asp Asn Glu Tyr Phe Tyr Val Asp Phe Arg Glu Tyr Asp Glu Tyr
                20                  25                  30
```

```
Phe Tyr Val Asp Phe Arg Glu Tyr Glu Tyr Asp Leu Lys Trp Glu Phe
            35                  40                  45

Pro Arg Glu Asn Leu Glu Phe Gly Lys Val Leu Gly Ser Gly Ala Phe
        50                  55                  60

Gly Lys Val Met Asn Ala Thr Ala Tyr Gly Ile Ser Lys Thr Gly Val
65                  70                  75                  80

Ser Ile Gln Val Ala Val Lys Met Leu Lys
                85                  90

<210> SEQ ID NO 9
<211> LENGTH: 25
<212> TYPE: DNA
<213> ORGANISM: Artificial Sequence
<220> FEATURE:
<223> OTHER INFORMATION: Description of Artificial Sequence: A primer
      for amplifying human FLT3/ITD genes

<400> SEQUENCE: 9
caacaattgg tgtttgtctc ctctt                                    25

<210> SEQ ID NO 10
<211> LENGTH: 25
<212> TYPE: DNA
<213> ORGANISM: Artificial Sequence
<220> FEATURE:
<223> OTHER INFORMATION: Description of Artificial Sequence: A primer
      for amplifying human FLT3/ITD genes.

<400> SEQUENCE: 10
catgatatct cgagccaatc caaag                                    25
```